United States Patent
DiSilvestro et al.

(10) Patent No.: US 7,769,422 B2
(45) Date of Patent: Aug. 3, 2010

(54) APPARATUS AND METHOD FOR MONITORING THE POSITION OF AN ORTHOPAEDIC PROSTHESIS

(75) Inventors: Mark R. DiSilvestro, Columbia City, IN (US); Jason T. Sherman, Leesburg, IN (US); Jose F. Guzman, Fort Wayne, IN (US); Edward J. Caylor, III, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 11/537,349

(22) Filed: Sep. 29, 2006

(65) Prior Publication Data
US 2008/0114270 A1      May 15, 2008

(51) Int. Cl.
*A61B 5/05* (2006.01)
*A61B 6/00* (2006.01)
*A61B 5/103* (2006.01)
*A61B 5/117* (2006.01)

(52) U.S. Cl. .................. 600/407; 600/415; 600/421; 600/431; 600/595; 623/11.11; 623/66.1

(58) Field of Classification Search .................. 600/424, 600/595, 407, 587, 415, 421, 422; 606/130; 342/463–465
See application file for complete search history.

(56) References Cited

U.S. PATENT DOCUMENTS

| | | | | |
|---|---|---|---|---|
| 2,548,671 A | * | 4/1951 | Kreer, Jr. ...................... | 342/432 |
| 3,824,595 A | * | 7/1974 | Hall ........................... | 342/432 |
| 5,211,165 A | * | 5/1993 | Dumoulin et al. ........... | 600/424 |
| 5,444,882 A | * | 8/1995 | Andrews et al. ............... | 5/618 |
| 5,729,129 A | * | 3/1998 | Acker ..................... | 324/207.12 |
| 5,879,297 A | | 3/1999 | Haynor | |
| 6,129,668 A | | 10/2000 | Haynor | |
| 6,198,963 B1 | * | 3/2001 | Haim et al. .................. | 600/424 |
| 6,216,028 B1 | | 4/2001 | Haynor | |
| 6,263,230 B1 | | 7/2001 | Haynor | |
| 6,366,799 B1 | * | 4/2002 | Acker et al. ................. | 600/424 |

(Continued)

FOREIGN PATENT DOCUMENTS

EP      1570782 A2      9/2005

(Continued)

OTHER PUBLICATIONS

Ryd, L., et al., Roentgen Stereophotogrammetric Analysis as a Predictor of Mechanical Loosening of Knee Prostheses, JBJS, 1995:3 (377-383).

(Continued)

*Primary Examiner*—Max Hindenburg
*Assistant Examiner*—John Pani
(74) *Attorney, Agent, or Firm*—Barnes & Thornburg LLP

(57) ABSTRACT

A system, apparatus, and method for determining a position of an orthopaedic prosthesis includes a patient support platform, a sensor array coupled to the patient support platform, and a controller electrically coupled to the sensor array. The sensor array is configured to generate data signals in response to an output signal of a signal source(s) coupled to the orthopaedic prosthesis and/or a bone of the patient. The controller is configured to determine a position of the orthopaedic prosthesis and/or the bone of the patient based on the data signals.

10 Claims, 7 Drawing Sheets

U.S. PATENT DOCUMENTS

| | | | |
|---|---|---|---|
| 6,772,002 B2 | 8/2004 | Schmidt et al. | |
| 7,030,612 B1 * | 4/2006 | Damadian et al. | 324/318 |
| 2004/0181149 A1 | 9/2004 | Langlotz et al. | |
| 2004/0243148 A1 | 12/2004 | Wasielewski | |
| 2005/0099290 A1 | 5/2005 | Govari | |
| 2007/0238982 A1 * | 10/2007 | Caylor, III | 600/424 |
| 2007/0270660 A1 * | 11/2007 | Caylor et al. | 600/300 |
| 2008/0125630 A1 * | 5/2008 | Caylor | 600/300 |

FOREIGN PATENT DOCUMENTS

| | | |
|---|---|---|
| EP | 2005086062 | 9/2005 |
| WO | 2005039440 | 5/2005 |
| WO | 2005/086062 | 9/2005 |
| WO | 20050087125 | 9/2005 |
| WO | WO 2005104976 A1 * | 11/2005 |

OTHER PUBLICATIONS

Karrholm, J., et al., Does Early Micromotion of Femoral Stem Prostheses Matter?, JBJS, 1994:6 (912-917).

Vrooman, et al., Fast and Accurate Automated Measurements in Digitized Stereophotogrammetric Radiographs, J. of Biomechanics, 1998 (491-498).

European Search Report for European Patent Application No. 07253846.5-2310, Jan. 30, 2008, 7 pgs.

* cited by examiner

APPARATUS AND METHOD FOR MONITORING THE POSITION OF AN ORTHOPAEDIC PROSTHESIS

TECHNICAL FIELD

The present disclosure relates generally to systems and methods for post-operatively monitoring the position of an orthopaedic prosthesis.

BACKGROUND

Orthopaedic implants or prostheses are implanted in patients by orthopaedic surgeons to, for example, correct or otherwise alleviate bone and/or soft tissue loss, trauma damage, and/or deformation of the bone(s) of the patients. Over time, the position of the orthopaedic prosthesis may change. For example, the orthopaedic prosthesis may migrate from the original implant location and/or subside into the supporting bony anatomy. In some cases, migration of the orthopaedic prosthesis may be an early indicator of implant loosening. As such, post-operative monitoring of the position of the orthopaedic prosthesis may provide an indication of potential difficulties that may develop over time.

SUMMARY

According to one aspect, an apparatus for monitoring the position of an orthopaedic prosthesis may include a patient support platform. The patient support platform may be configured to support a patient in a standing position. In some embodiments, the patient support platform may be embodied as an enclosure having an interior space defined therein. The apparatus may also include a sensor array coupled to the patient support platform. The sensor array may be configured to generate data signals in response to an output signal received from a signal source coupled to the orthopaedic prosthesis. In some embodiments, the signal source may be embodied as one or more magnetic sources. In such embodiments, the sensor array may include a plurality of magnetic sensors. The magnetic sensors may be configured to generate data signals in response to a magnetic field generated by the magnetic source(s). In other embodiments, the signal source may be embodied as one or more wireless transmitters. In such embodiments, the sensor array may include a plurality of antennas configured to generate data signals in response to an output signal received from the wireless transmitter(s). The plurality of antennas may include, for example, a plurality of first antennas positioned substantially coplanar with each other and at least one second antenna positioned non-coplanar with respect to the plurality of first antennas. The antennas may be, for example, spiral directional antennas. In such embodiments, the plurality of first antennas may be positioned such that a boresight of each first antenna is directed toward a common volume of space and the second antenna may be positioned such that a boresight of the second antenna is directed toward the common volume of space.

The apparatus may also include means for securing at least a portion of the patient's body in a fixed position relative to the sensor array while the patient is supported by the patient support platform. The means for securing the patient may include, for example, one or more pads coupled to a support frame of the apparatus and movable with respect to the support frame to secure at least a portion of the patient in a fixed position relative to the patient support platform. The apparatus may also include a controller electrically coupled to the sensor array. In embodiments wherein the patient support platform is embodied as an enclosure, the controller or portion thereof may be positioned in the enclosure. The controller may be configured to determine a position of the orthopaedic prosthesis based on the data signals received from the sensor array. To do so, in some embodiments, the controller may be configured to determine the position of the orthopaedic prosthesis by comparing the data signals to each other. The apparatus may further include a display device coupled to the patient support platform and electrically coupled to the controller. In such embodiments, the controller may be configured to display indicia of the location of the orthopaedic prosthesis on the display device. The controller may also be configured to retrieve position data indicative of a previously determined position of the orthopaedic prosthesis from a storage device and display indicia of the previously determined position of the orthopaedic prosthesis on the display device.

According to another aspect, a system for monitoring the position of an orthopaedic prosthesis may include a patient support platform. The patient support platform may be configured to support the patient in a standing position. The system may also include a first signal source configured to be coupled to the orthopaedic prosthesis and generate a first output signal when the patient is standing on the patient support platform. The first signal source may be, for example, a magnetic source or a wireless transmitter. The apparatus may also include a sensor array coupled to the patient support platform. The sensor array may be configured to generate data signals in response to the first output signal received from the first signal source. In embodiments wherein the signal source is embodied as one or more magnetic sources, the sensor array may be embodied as a number of magnetic sensors. In embodiments wherein the signal source is embodied as one or more wireless transmitters, the sensor array may be embodied as a plurality of antennas. In such embodiments, the plurality of antennas may include a plurality of first antennas each being positioned substantially coplanar with each other and at least one second antenna positioned non-coplanar with respect to the plurality of first antennas.

The system may also include a controller. The controller may be electrically coupled to the sensor array. The controller may be configured to determine a present position of the orthopaedic prosthesis based on the data signals received from the sensor array. For example, the controller may be configured to determine the location of the orthopaedic prosthesis with respect to the patient support platform. The controller may also be configured to retrieve position data indicative of a previously determined position of the orthopaedic prosthesis from a storage device. Additionally, the controller may be configured to display indicia of the present position and the previously determined position of the orthopaedic prosthesis on a display device. In some embodiments, the system may further include a second signal source configured to be coupled to a first component of the orthopaedic prosthesis and generate a second output signal when the patient is standing on the patient support platform. In such embodiments, the first signal source may be configured to be coupled to a second component of the orthopaedic prosthesis. The controller may be configured to determine the position of the first component and the second component of the orthopaedic prosthesis with respect to each other based on data signals received from the sensor array in response to the first and the second output signals. In another embodiment, the second signal source may be configured to be coupled to a bone of the patient. In such embodiments, the controller may be configured to determine the position of the bone of the patient and the orthopaedic prosthesis with respect to each other based on data signals received from the sensor array in response to the first and the second output signals.

According to a further aspect, an apparatus for monitoring the position of an orthopaedic prosthesis may include a patient support platform configured to support a patient in a standing position. The apparatus may also include a support frame coupled to the patient support platform and a display device coupled to the support frame. Additionally, the apparatus may include a plurality of pads coupled to the support frame. The plurality of pads may be movable with respect to the support frame to secure at least a portion of the patient in a fixed position. The apparatus may also include a sensor array coupled to the support frame. The sensor array may be configured to generate data signals in response to an output signal received from a signal source coupled to the orthopaedic prosthesis. In some embodiments, the signal source may be embodied as one or more magnetic sources. In such embodiments, the sensor array may include a plurality of magnetic sensors. In other embodiments, the signal source may be embodied as one or more wireless transmitters. In such embodiments, the sensor array may include a plurality of antennas. The apparatus may further include a controller electrically coupled to the sensor array. The controller may be configured to determine a position of the orthopaedic prosthesis based on the data signals received from the sensor array and display indicia of the position of the orthopaedic prosthesis on the display device. In some embodiments, the apparatus may also include a display device coupled to the support frame and electrically coupled to the controller. In such embodiments, the controller is configured to display indicia of the location of the orthopaedic prosthesis on the display device. Additionally, in such embodiments, the controller may be configured to retrieve position data indicative of a previously determined position of the orthopaedic prosthesis from a storage device and display indicia of the previously determined position of the orthopaedic prosthesis on the display device.

BRIEF DESCRIPTION OF THE DRAWINGS

The detailed description particularly refers to the following figures, in which.

DETAILED DESCRIPTION OF THE DRAWINGS

Figure 1:
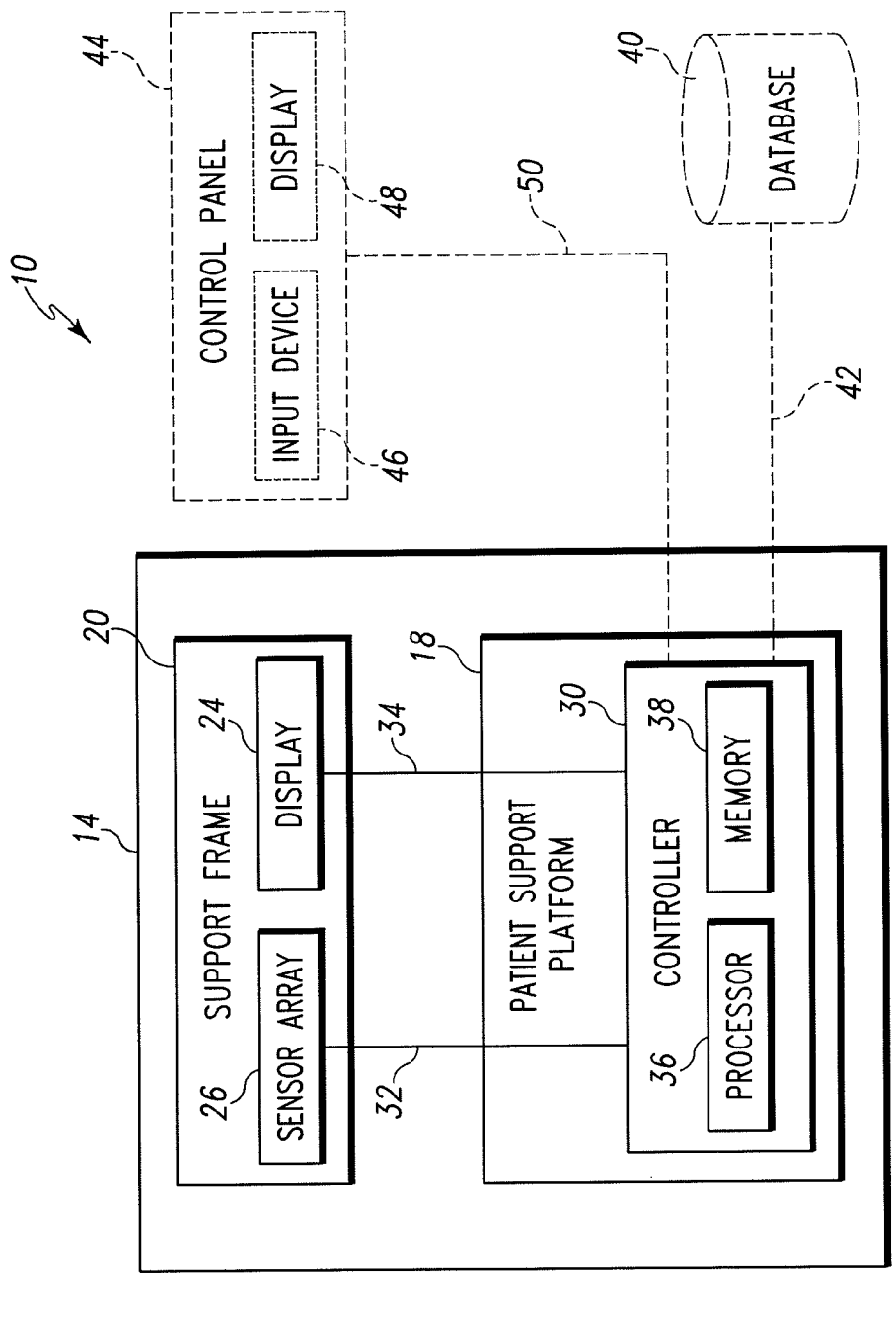
FIG. 1 is a simplified diagram of a system for monitoring the position of an orthopaedic prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a system 10 for monitoring the position of an orthopaedic prosthesis 12 includes a patient support apparatus 14 configured to support a patient 16 thereon. The patient support apparatus 14 includes a patient support platform 18 and a support frame 20. The patient support platform 18 may be embodied as any type of platform having a generally planar surface 22 (see FIGS. 2 and 3) capable of supporting the patient 16 in a standing position. As such, the patient support platform 18 may be formed from any material capable of supporting the patient 16 such as, for example, a non-ferrous metallic material, a plastic material, wood, or the like. The support frame 20 is coupled to the patient support platform 18 and provides a structure for the patient 16 to grasp and/or hold during the operation of the system 10. In addition, the support frame 20 provides a structure to which other components of the apparatus 14 may be coupled as described below. The support frame 20 may have any configuration based on, for example, characteristics of the intended patients, the number and type of components included in the apparatus 14, the particular implementation of the apparatus 14, and/or the like. In some embodiments, the support frame 20 may be adjustable to accommodate patients of different heights, movability, and the like.

The apparatus 14 also includes a display device 24 and a sensor array 26 coupled to the support frame 20. The display device 24 may be embodied as any device capable of displaying images and information to the patient 16 and/or an orthopaedic healthcare provider such as an orthopaedic surgeon or nurse. In one particular embodiment, the display device 24 is embodied as a display monitor such as a liquid crystal display (LCD) monitor. The sensor array 26 may be embodied as any device or collection of devices capable of sensing, receiving, or otherwise detecting output signals from one or more signal sources 28 coupled to one or more components of the orthopaedic prosthesis 12 and/or a bone(s) of the patient 16. In one embodiment, as discussed in more detail below in regard to FIG. 2, the signal source(s) 28 is embodied as a number of magnetic sources such as permanent magnets. In such embodiments, the sensor array 26 is embodied as a number of magnetic sensors configured to sense a magnetic field generated by the magnetic source(s) and generate data signals indicative of a position of the magnetic source(s) relative to the sensor array 26. In another embodiment, as discussed in more detail below in regard to FIG. 3, the signal source(s) 28 is embodied as a number of wireless transmitters. In such embodiments, the sensor array 26 is embodied as a number of antennas configured to receive output signals of the wireless transmitters and generate data signals indicative of a position of the wireless transmitter(s) relative to the sensor array 26.

It should be understood that, as used herein, the term "position" is intended to refer to any one or more of the six degrees of freedom which define the location and orientation of a body in space relative to a predetermined reference point or other body. For example, the position of a body may be defined by an X-coordinate value, a Y-coordinate value, a Z-coordinate value, a first rotational value about the X-axis, a second rotational value about the Y-axis, and/or a third rotational value about the Z-axis value of the body relative to a predetermined reference point or other body. For example, the orthopaedic prosthesis 12 and/or bone of the patient 16 may have a position defined by one or more of the above-described six degrees of freedom values relative to the sensor array 26, the patient support platform 18, or the patient support apparatus 14.

The patient support apparatus 14 also includes a controller 30 communicatively coupled to the sensor array 26 via a number of communication links 32 and to the display 24 via a number of communication links 34. The communication links 32, 34 may be embodied as any type of communication links capable of facilitating electrical communication between the controller 30 and the sensor array 26 and the display 24, respectively. For example, the communication links 32, 34 may be embodied as any number of wires, cables, or the like.

The controller 30 includes a processor 36 and a memory device 38. The processor 36 may be embodied as any type of processor including, for example, discrete circuitry (e.g., a collection of logic devices), general purpose integrated circuit(s), and/or application specific integrated circuit(s) (i.e., ASICs). The memory device 48 may be embodied as any type of memory device and may include one or more memory types, such as, random access memory (i.e., RAM) and/or read-only memory (i.e., ROM). In addition, the controller 30 may include other devices and circuitry typically found in a computer or computing device for performing the functions described herein such as, for example, a hard drive, input/output circuitry, and/or the like.

In use, the controller 30 receives data signals from the sensor array 26 indicative of the position of the signal source(s) 28 while the patient 16 is supported by the patient support platform 18. The controller 30 is configured to determine the position (e.g., the location and orientation) of the orthopaedic prosthesis 12 and/or bones of the patient to which the signal source(s) 28 is/are coupled based on the data signals. The controller 30 may use any suitable algorithm to determine the position of the orthopaedic prosthesis and/or bone of the patient. For example, as discussed in more detail below in regard to FIG. 2, the controller 30 may be configured to determine the position of the orthopaedic prosthesis 12 and/or bones of the patient by performing an optimization algorithm on the data signals received from the sensor array 26 in those embodiments wherein the signal source(s) 28 are embodied as magnetic sources and the sensor array 26 is embodied as a magnetic sensor array. Alternatively, as discussed in more detail below in regard to FIG. 3, the controller 30 may be configured to determine the position of the orthopaedic prosthesis 12 and/or bones of the patient by using a radio frequency (RF) direction finding algorithm in those embodiments wherein the signal source(s) 28 are embodied as wireless transmitters and the signal array 26 is embodied as a plurality of antennas.

Additionally, depending on the particular application, the controller 30 may be configured to determine the position of the orthopaedic prosthesis 12 and/or bones of the patient relative to a predetermined coordinate system. For example, in some embodiments, the controller 30 may be configured to determine the position of the orthopaedic prosthesis 12 with respect to the patient support apparatus 14 (e.g., the patient support platform 18) as discussed in more detail below in regard to FIG. 5. In such embodiments, the change of the location and/or orientation of the orthopaedic prosthesis 12 relative to the patient support apparatus 14 may be monitored over time. Alternatively, in embodiments wherein a signal source 28 is coupled to each relevant component of an orthopaedic prosthesis 12 (e.g., a signal source 28 may be coupled to a tibial component and a femoral component of a knee prosthesis), the controller 30 may be configured to determine the position of each component of the orthopaedic prosthesis 12 with respect to each other as discussed in more detail below in regard to FIG. 6. In such embodiments, the change in relative position between the components may be monitored over time. Further, in embodiments wherein a signal source 28 is coupled to one or more components of the orthopedic prosthesis 12 and one or more signal sources 28 are coupled to a bone of the patient 16, the controller 30 may be configured to determine the position of the orthopaedic prosthesis 12 (or component thereof) and the relevant bone(s) of the patient with respect to each other as discussed in more detail below in regard to FIG. 7. In such embodiments, the change in relative position between the orthopaedic prosthesis 12 and the relevant bone of the patient 16 may be monitored over time. Regardless, once the controller 30 has determined the position of the orthopaedic prosthesis 12 and/or bone(s) of the patient 16, the controller 16 may be configured to display indicia of the position of the prosthesis 12 and/or bones, such as images, graphs, symbols, or the like, on the display device 24 such that the position may be viewed by the patient 16 and/or an orthopaedic healthcare provider.

It should be appreciated that the orthopaedic prosthesis 12 may be embodied as any type of orthopaedic prosthesis formed from any number of orthopaedic prosthesis components. For example, the orthopaedic prosthesis 12 may be embodied as a knee prosthesis, a hip prosthesis, a shoulder prosthesis, an ankle prosthesis, or any other joint replacement prosthesis as well as any type of orthopaedic trauma implant such as a plate, nail, or the like. As discussed above, one or more of the components of the orthopaedic prosthesis may include a signal source 28 coupled thereto. For example, in those embodiments wherein the orthopaedic prosthesis 12 is embodied as a knee prosthesis, the tibial component and/or the femoral component of the orthopaedic prosthesis 12 may include a signal source 28 coupled thereto. As such, it should be appreciated that the system 10 is usable with any type of orthopaedic prosthesis capable of having a suitable signal source 28 coupled to one or more components thereof.

In the illustrative embodiment of FIG. 1, the controller 30 is coupled to or otherwise housed in the patient support apparatus 14. For example, in some embodiments, the patient support platform 18 is embodied as an enclosure having an interior chamber or space. In such embodiments, the controller 30, or portion thereof, may be housed in the interior chamber or space of the patient support platform 18. Alternatively, the controller 30, or portion thereof, may be located remotely from the patient support platform 30 and/or apparatus 14.

In some embodiments, the system 10 may also include a remote database 40. The database 40 may be embodied as any type of database, electronic library, and/or file storage location. For example, the database 40 may be embodied as a structured database or as an electronic file folder or directory containing a number of separate files and an associated "look-up" table. Further, the database 40 may be stored on any suitable device. For example, the database 40 may be stored in a set of memory locations of a remote computer and/or a stored on a separate storage device such as a hard drive or the like.

The database 40 is communicatively coupled to the controller 30 via a number of communication links 42. The communication links 42 may be embodied as any type of communication links capable of facilitating electrical communication between the controller 30 and database 40. For example, the communication links 42 may be embodied as any number of wires, cables, or the like. Additionally, the communication links 42 may form a portion of a communication network such as, for example, a Local Area Network (LAN), a Wide Area Network (WAN), and/or a global, publicly-accessible network such as the Internet.

In use, the controller 30 may be configured to store position data indicative of the determined position of the orthopaedic prosthesis 12 and/or bones of the patient in the database 40. Additionally, in some embodiments, the controller 30 may be configured to retrieve historical position data (i.e., data indicative of the position of the orthopaedic prosthesis 12 and/or bones of the patient as determined during a prior examination of the patient using the system 10). In such embodiments, the controller 30 may also be configured to display indicia of the previously determined positions of the prosthesis 12 and/or bones, such as images, graphs, symbols, or the like, on the display device 24. If so, such indicia of the previously determined positions may be displayed contemporaneously with the indicia indicative of the present position of the orthopaedic prosthesis 12 and/or bones of the patient such that a comparison between the present positions and the historical position(s) may be performed by an orthopaedic healthcare provider.

The system 10 may also include a remote control panel 44 in some embodiments. The control panel 44 may be located remotely from the apparatus 14 such as in a separate room of a healthcare facility or otherwise apart from the patient support apparatus 14. The remote control panel 44 is communicatively coupled to the controller 30 via a number of communication links 50. The communication links 50 may be embodied as any type of communication links capable of facilitating electrical communication between the controller 30 and remote control panel 44. For example, the communication links 50 may be embodied as any number of wires, cables, or the like.

The control panel 44 may be used by an orthopaedic healthcare provider, such as an orthopaedic surgeon, to control the operation of the patient support apparatus 14. To do so, the orthopaedic healthcare provider may operate an input device 46 of the remote control panel 44 to supply information, directions, and/or responses to the controller 30 via the communication links 50. For example, the orthopaedic healthcare provider may instruct the controller 30 when the measurement process should begin (e.g., when the patient has successfully mounted the patient support platform 18). Additionally, the controller 30 may be configured to display indicia of the determined position of the orthopaedic prosthesis 12 and/or bone(s) of the patient 16, as well as indicia of any previously determined positions retrieved from the database 40, on the display device 48 via the communication links 50. In this way, an orthopaedic healthcare provider may operate the apparatus 14 and monitor data determined by the controller 30 using the remote control panel 44.

Figure 2:
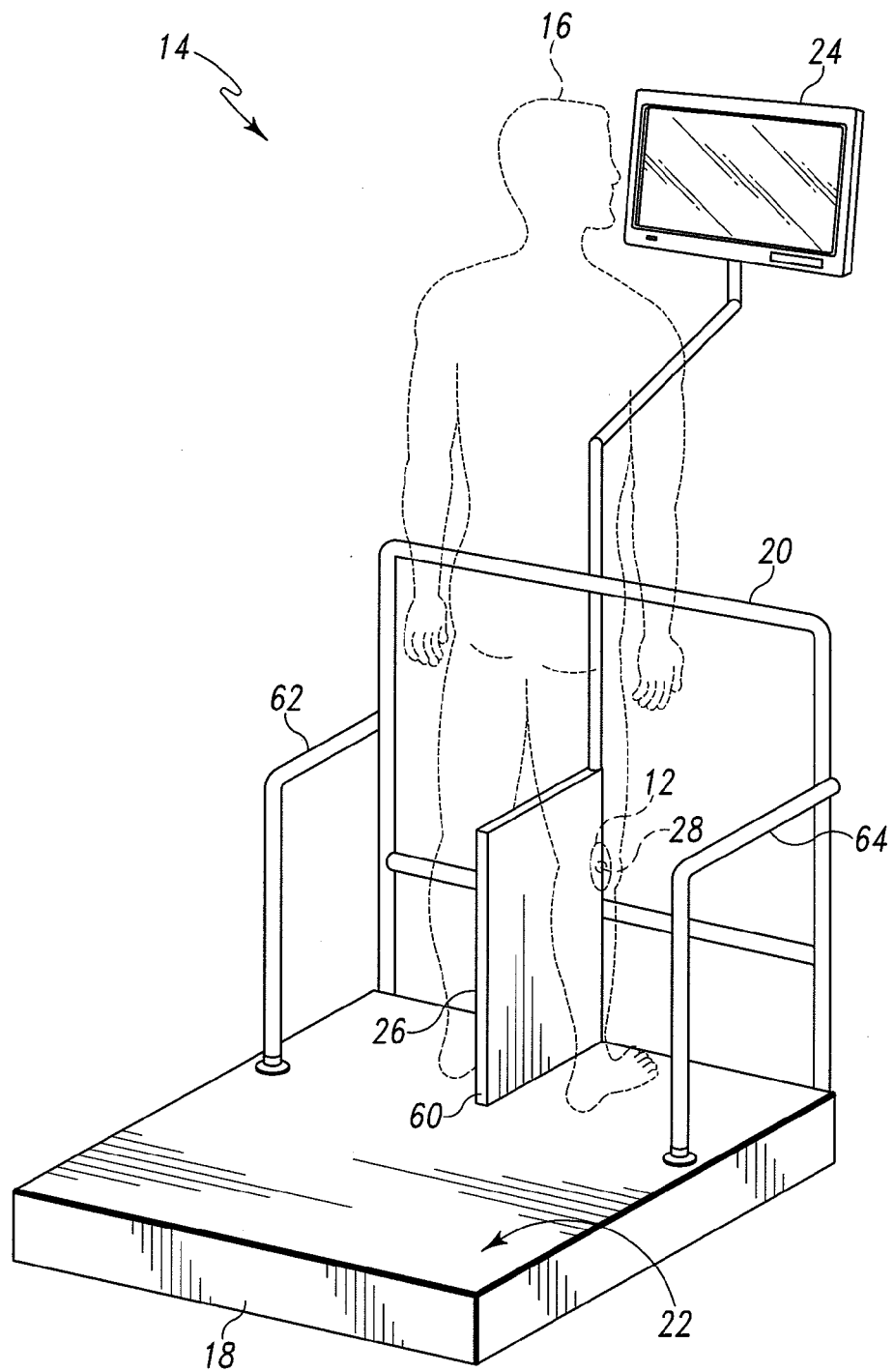
FIG. 2 is a perspective view of one embodiment of a patient support apparatus of the system of FIG. 1.

Referring now to FIG. 2, in some embodiments the signal source(s) 28 may be embodied as a number of magnetic sources, such as permanent magnets, as discussed above in regard to FIG. 1. The magnetic signal source(s) 28 may be coupled to one or more components of the orthopaedic prosthesis 12 and/or one or more relevant bones of the patient 16. In such embodiments, the sensor array 28 is embodied as a magnetic sensor array 60. The magnetic sensor array 60 is formed from a number of magnetic sensors, which may be positioned in a predetermined configuration to thereby sense or measure one or more components of the three dimensional magnetic field generated by the magnetic signal source(s) 28. The particular number of magnetic sensors used to form the magnetic sensor array 60 may depend on such criteria as the type of magnetic sensors, the specific application, and/or the configuration of the magnetic sensor array 60. The magnetic sensor array 60 may include any number and configuration of one-dimensional, two-dimensional, and/or three-dimensional magnetic sensors such that the magnetic sensor array 60 is capable of sensing or measuring the magnetic field of the magnetic signal source(s) 28 implanted in the patient 16 when the patient is standing on the patient support platform 18. Additionally, the magnetic sensor(s) may be embodied as any type of magnetic sensor capable of sensing or measuring the magnetic field generated by the magnetic signal source 28. For example, the magnetic sensors may be embodied as one or more superconducting quantum interference (SQUID) magnetic sensors, anisotropic magnetoresistive (AMR) magnetic sensors, giant magnetoresistive (GMR) magnetic sensors, Hall-effect magnetic sensors, or any other type of magnetic sensors capable of sensing or measuring the three-dimensional magnetic field of the magnetic source.

As such, the magnetic sensor array 60 may be embodied as any type of magnetic sensor array capable of sensing or measuring a magnetic field generated by the magnetic signal source(s) 28. For example, the magnetic sensor array 60 may be embodied as one of the magnetic sensor arrays described in detail in U.S. patent application Ser. No. 11/323,609, entitled "APPARATUS AND METHOD FOR REGISTERING A BONE OF A PATIENT WITH A COMPUTER ASSISTED ORTHOPAEDIC SURGERY SYSTEM", which was filed on Dec. 30, 2005 by Jason T. Sherman et al.; in U.S. patent application Ser. No. 11/323,963, entitled "SYSTEM AND METHOD FOR REGISTERING A BONE OF A PATIENT WITH A COMPUTER ASSISTED ORTHOPAEDIC SURGERY SYSTEM," which was filed on Dec. 30, 2005 by Jason T. Sherman et al.; in U.S. patent application Ser. No. 11/323,610, entitled "MAGNETIC SENSOR ARRAY," which was filed on Dec. 30, 2005 by Jason T. Sherman et al.; and/or in U.S. patent application Ser. No. 11/323,537, entitled "METHOD FOR DETERMINING A POSITION OF A MAGNETIC SOURCE," which was filed on Dec. 30, 2005 by Jason T. Sherman et al., the entirety of all of which is expressly incorporated herein by reference.

In the illustrative embodiment of FIG. 2, the magnetic sensor array 60 is coupled to the support frame 20 and the patient support platform 18. The magnetic sensor array 60 is centrally located on the surface 22 of the patient support platform 18 such that the magnetic sensor array 60 is positioned between the legs of the patient 16 while the patient 16 is standing on the patient support platform 18. In this way, the magnetic sensor array 60 is positioned in a location for sensing the magnetic field(s) generated by the magnetic signal source(s) 28 located in the region of the knee of the patient 16. For example, the apparatus 14 illustrated in FIG. 2 may be used in embodiments wherein the orthopaedic prosthesis 12 is embodied as a knee prosthesis. In other embodiments, such as those embodiments wherein the orthopaedic prosthesis 12 is embodied as a hip prosthesis or a shoulder prosthesis, the magnetic sensor array 60 may be coupled to the patient support platform 18 and support frame 20 in a different location. For example, in embodiments wherein the orthopaedic prosthesis 12 is embodied as a hip prosthesis, the magnetic sensor array 60 may be coupled a side rail 62, 64 of the support frame 20 in an elevated position relative to the magnetic sensor array 60 illustrated in FIG. 2. Additionally, the apparatus 14 may include more than one magnetic sensor arrays 60 in some embodiments. For example, the apparatus 14 may include a magnetic sensor array 60 coupled to each of the side rails 62, 64. Additionally or alternatively, the magnetic sensor array 60 may be configured to be positionable in one or a number of locations on the support frame 20 and/or patient support platform 18 such that the magnetic sensor array 60 may be relocated based on the type of orthopaedic prosthesis 12 being monitored.

Figure 3:
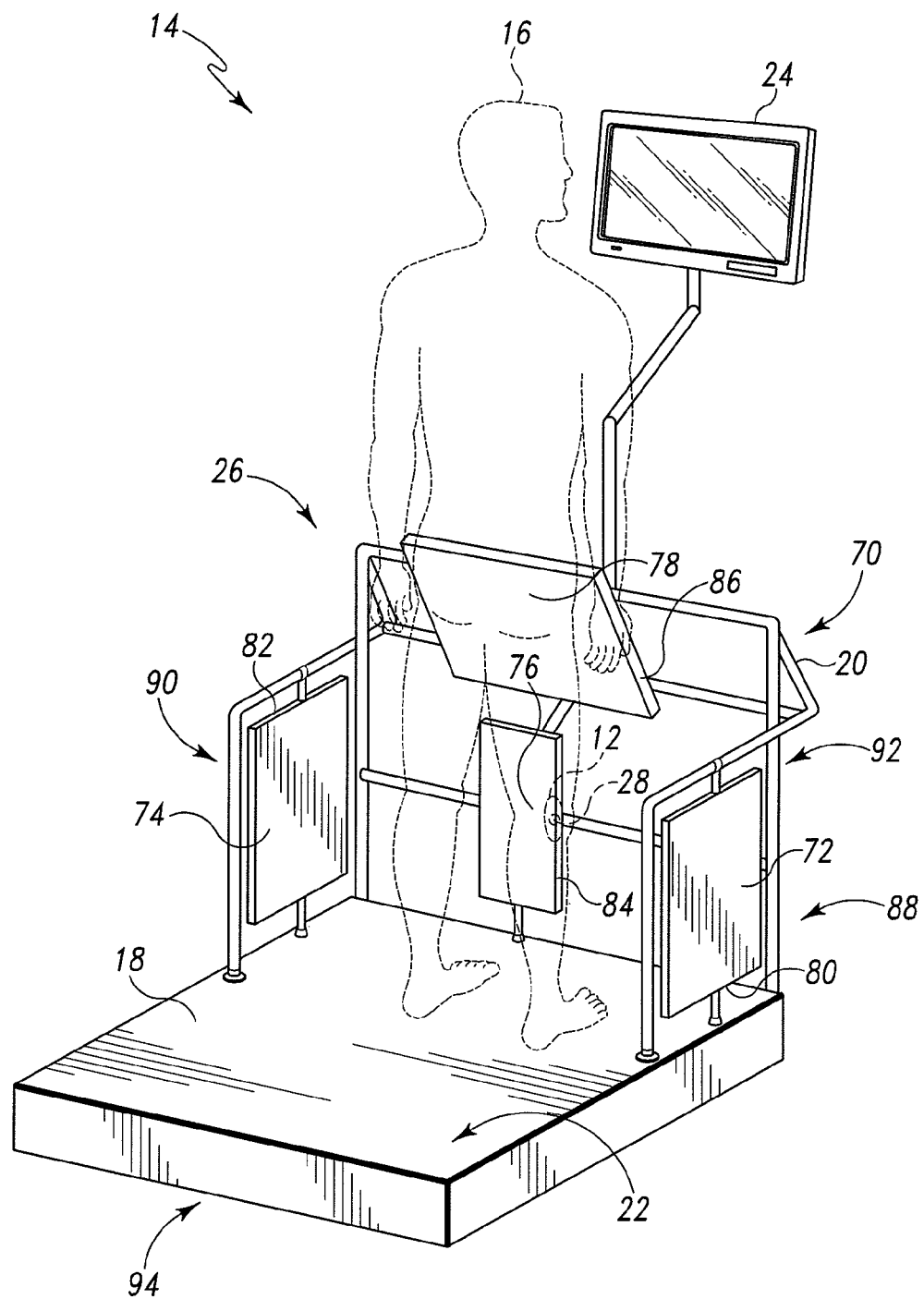
FIG. 3 is a perspective view of another embodiment of the patient support apparatus of the system of FIG. 1.

Referring now to FIG. 3, in some embodiments the signal source(s) 28 may be embodied as a number of wireless transmitters as discussed above in regard to FIG. 1. The wireless transmitters may be coupled to one or more components of the orthopaedic prosthesis 12 and/or one or more relevant bones of the patient 16. The wireless transmitters may be configured to transmit a wireless signal at a predetermined frequency or a predetermined pulse repetition frequency. In some embodiments, the wireless signal generated by the wireless transmitters is a non-modulated wireless signal. That is, the wireless signal does not include other signals (e.g., data signals) embedded or modulated in the predetermined carrier frequency. In other embodiments, the wireless signal generated by the wireless transmitters is a modulated wireless signal having a serial number associated with the wireless transmitted modulated on a predetermined carrier frequency. The predetermined frequency of the wireless signal may be any frequency receivable by the sensor array 26 such as, for example, a frequency or range of frequencies in the very-high frequency (VHF) band or ultra-high frequency (UHF) band.

In such embodiments, the sensor array 26 is embodied as an antenna array 70. The antenna array 70 includes a number of coplanar antennas 72, 74, 76 and at least one non-coplanar antennas 78 (with respect to the coplanar antennas 72, 74, 76). The antennas 72, 74, 76, 78 are directional antennas having a radiation/receiving pattern that is not omni-directional. For example, the antennas 72, 74, 76, 78 may be unidirectional antennas. In one particular embodiment, the antennas 72, 74, 76, 78 are spiral directional antennas. The directivity of each directional antenna 72, 74, 76, 78 is defined by the beamwidth the antenna 72, 74, which is defined about the boresight of each antenna 72, 74, 76, 78. The boresight of the antenna 72, 74, 76, 78 typically corresponds to a physical axis of the antenna and is defined as the axis of the antenna 72, 74, 76, 78 along which the gain of the antenna 72, 74, 76, 78 is greatest. As such, the antennas 72, 74, 76, 78 are sensitive to signals generated by sources positioned in the antenna's 72, 74, 76, 78 beamwidth. Conversely, signals incoming toward the antennas 72, 74, 76, 78 from sources outside of the beamwidth of the antennas 72, 74, 76, 78 are substantially attenuated.

As such, the antenna array 70 may be embodied as any type of antenna array having a number of co-planar antennas and at least one non-coplanar antenna. For example, the antenna array 70 may be embodied as one of the antenna arrays described in detail in U.S. patent application Ser. No. 11/391,840, entitled "SYSTEM AND METHOD FOR DETERMINING A LOCATION OF AN ORTHOPAEDIC MEDICAL DEVICE," which was filed on Mar. 29, 2006 by Edward J. Caylor III, et al. and/or in U.S. patent application Ser. No. 11/392,001, entitled "SYSTEM AND METHOD FOR MONITORING KINEMATIC MOTION OF A PATIENT," which was filed on Mar. 29, 2006 by Edward J. Caylor III, the entirety of each of which is expressly incorporated herein by reference.

In the illustrative embodiment of FIG. 3, the coplanar antennas 72, 74, 76 and the non-coplanar antenna 78 are coupled to the support frame 20 of the apparatus 14. To do so, the antennas 72, 74, 76, 78 are positioned in housings 80, 82, 84, 86, respectively, which are coupled to a frame 20 of the patient support apparatus 14. That is, the first housing 80, and thereby the coplanar antenna 72, is coupled to the support frame 20 of the patient support apparatus 14 on a first longitudinal side 88. The second housing 82, and thereby the coplanar antenna 74, is coupled to the support frame 20 on a second longitudinal side 90 of the patient support apparatus 14. The third housing 84, and thereby the coplanar antenna 76, is coupled to the support frame 20 on a front side 92 of the patient support apparatus 14. The housings 80, 82, 84 are coupled to the support frame 20 such that the antennas 72, 74, 76 are positioned coplanar with respect to each other. Additionally, the antennas are positioned such that the boresight of each antenna 72, 74, 76 is directed inwardly toward the area of the patient support platform 18 wherein the patient 16 is to stand. That is, the antenna 72 is positioned such that the boresight of the antenna 72 is directed toward the opposite longitudinal side 90 of the patient support apparatus 14. Similarly, the antenna 74 is positioned such that the boresight of the antenna 74 is directed toward the opposite longitudinal side 88. The antenna 76 is positioned such that the boresight of the antenna 76 is directed toward a rear side 94 of the patient support apparatus 14.

The beamwidths of the antennas 72, 74, 76 define a common volume of space in which the relevant portion(s) of the patient 16 (i.e., the portion of the patient 16 wherein the orthopaedic prosthesis 12 is implanted) is positioned when the patient 16 is supported by the patient support platform 18. For example, if the relevant portion of the patient is a knee area, the antennas 72, 74, 76 are positioned such that the relevant knee and surrounding area of the patient 16 is positioned in the common volume of space defined by the beamwidths of the antennas 72, 74, 76. To facilitate various areas of interest of the patient 16, in some embodiments, the housings 80, 82, 84 are movably coupled to the support frame 20 such that the housings 80, 82, 84 may be moved to different positions to thereby move the common volume of space such that the relevant portion of the patient 16 is positioned therein. For example, the housings 80, 82, 84 may be movably coupled to the support frame 20 such that the housings 80, 82, 84 may be moved vertically up or down as required based on the location of the orthopaedic prosthesis 12.

The housing 86 is also coupled to the support frame 20. The housing 86 is so coupled such that the antenna 78 is positioned non-coplanar with respect to the antennas 72, 74, 76 but is directed toward the reference plane defined by the antennas 72, 74, 76. That is, the antenna 78 is coupled to the support frame 20 such that the beamwidth of the antenna 78 is directed toward the common volume of space defined by the beamwidths of the antennas 72, 74, 76. Similar to the housings 80, 82, 84, the housing 86 may be movably coupled to the support frame 20 such that the housing 86 may be moved to different positions to thereby move the common volume of space such that the relevant portion of the patient 16 is positioned therein.

Figure 4:
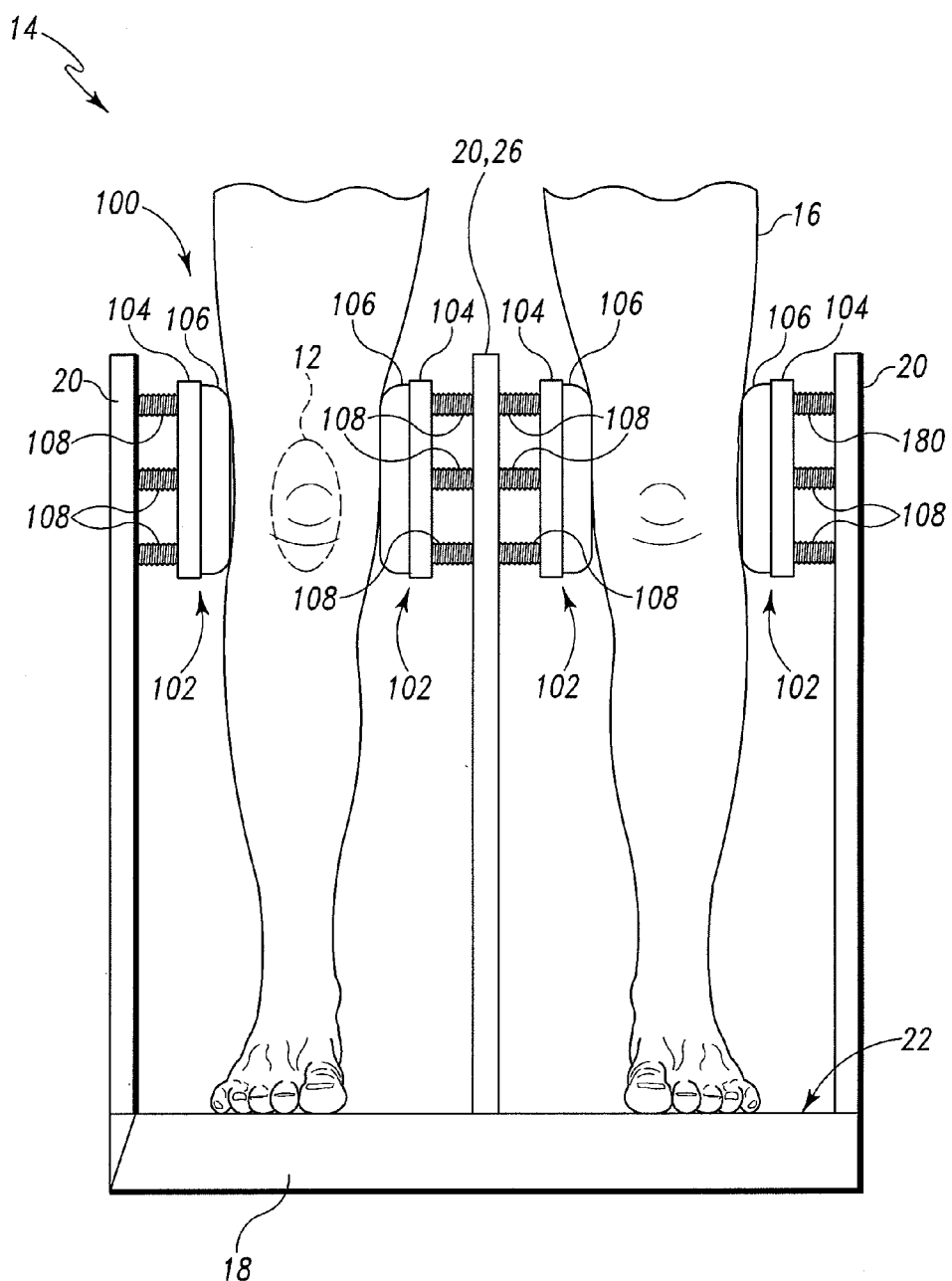
FIG. 4 is an elevation view of one embodiment of a securing device for securing a patient in a fixed position on the patient support apparatus of FIG. 1.

Referring now to FIG. 4, in some embodiments, the apparatus 14 may include a jig 100 for securing the patient 16, or a portion of the patient 16 such as a leg, in a fixed position relative to the patient support apparatus 14. Depending on the particular location of the orthopaedic prosthesis 12 in the patient 16, the jig 100 or components thereof may be movably secured to the patient support apparatus 14 in a number of locations. In one particular embodiment, as illustrated in FIG. 4, the jig 100 is embodied as a number of pads 102 movably coupled to the support frame 20 such that each pad 102 is extendable relative to the support frame 20. Each of the pads 102 includes a substrate 104 and a padding surface 106. The substrate 104 may be formed from any material rigid enough to support the padding surface 106 in a compressed state against the body of the patient 16. The pads 102 are movably coupled to the support frame 20 via a number of threaded screws 108. The pads 102 may be extended from or toward the support frame 20 by adjusting the screws 108. In this way, the patient 16, or portion of the patient 16 such as a leg, may be secured in a fixed position by adjusting the screws 108 to extend the pads 102 toward the body of the patient 16. Because both sets of pads 102 are extendible toward each other, the pads 102 may be extended until each pad 102 applies enough pressure on the body of the patient 16 to secure the relevant portion of the patient 16 in a fixed position.

It should be appreciated that in embodiments wherein the controller 30 is configured to determine the position of the orthopaedic prosthesis 12, or component thereof, the relevant portion of the patient 16 is secured in a fixed position that is similar to the position of the patient during previous examinations. In this way, any change in the position of the orthopaedic prosthesis 12 is attributable to a change in the position of the prosthesis 12 relative to the patient rather than a change in the position of the patient 16 relative to the patient support platform 18.

Although the jig 100 is illustrated and described as a number of movable pads in regard to FIG. 4, it should be appreciated that other jigs may be used to secure the patient 16, or portion thereof, in a fixed position relative to the platform 18 in other embodiments. For example, a number of straps may be used to secure a portion, such as a leg, of the patient 16 in a fixed position relative to the patient support apparatus 14. In other embodiments, the jig 100 may be embodied as a brace such as a leg brace, a receptacle configured to receive the relevant portion of the patient, and/or the like. Additionally, in some embodiments, the top surface 22 of the patient support platform 18 may include markings or other indications of the location in which the patient is to stand (e.g., the location in which the patient 16 should place his/her feet).

Figure 5:
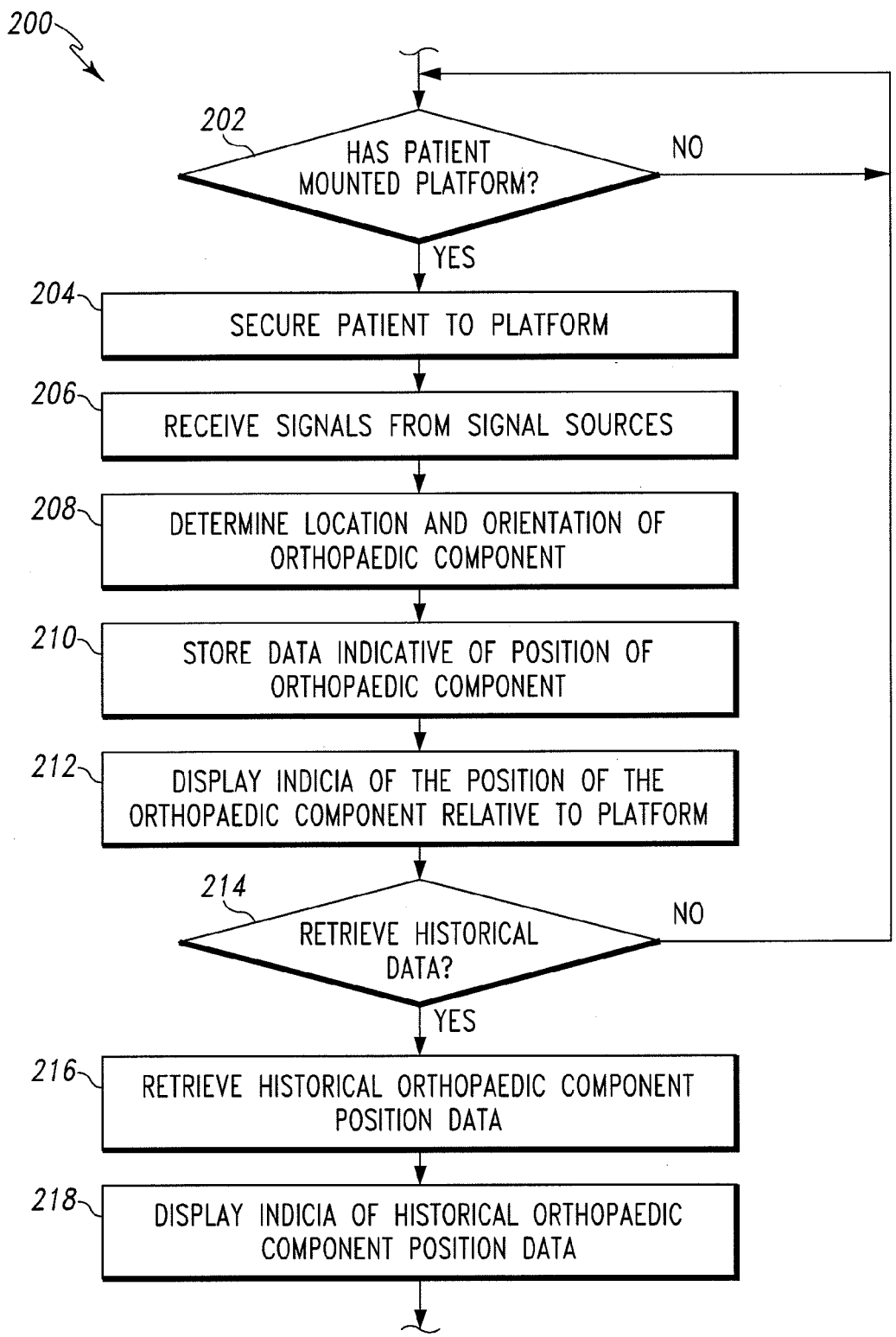
FIG. 5 is a simplified flowchart of one embodiment of an algorithm for determining a position of an orthopaedic prosthesis executed by the system of FIG. 1.

Referring now to FIG. 5, in embodiments wherein the controller 30 is configured to determine the position of the orthopaedic prosthesis 12 relative to the patient support apparatus 14 (e.g., relative to the patient support platform 18 or the sensor array 26), the controller 30 may be configured to execute an algorithm 200 for determining the position of the orthopaedic prosthesis 12 or component(s) thereof. In such embodiments, each component of interest of the orthopaedic prosthesis 12 includes one or more signal sources 28 coupled thereto. As discussed above in regard to FIGS. 1-3, such signal sources 28 may be embodied as a number of magnetic sources or a number of wireless transmitters.

The algorithm 200 beings with a process step 202 in which the controller 30 determines if the patient 16 has mounted the patient support platform 18. To do so, the patient support platform 18 may include a number of sensors, such as pressure sensors, for detecting when the patient 16 has mounted the platform 18. Alternatively, the orthopaedic healthcare provider may instruct the controller 30 that the patient has successfully mounted the patient support platform 18 by, for example, selecting an appropriate button, entering a predetermined command, or the like via the input device 46.

Once the controller 30 has determined that the patient 16 has mounted the patient support platform 18, the patient 16 is secured in a fixed position on the platform 18 in process step 204. That is, the portion of the patient 16 wherein the orthopaedic prosthesis 12 and/or any bone(s) of interest are located is secured in a fixed position relative to the patient support apparatus 14. To do so, the jig 100 may be used to secure the patient 16. For example, in embodiments wherein the jig 100 is embodied as the pads 102 illustrated in FIG. 4, the screws 108 may be operated to extend the pads 102 in an outward direction relative to the support frame 20 to thereby apply a securing pressure on the relevant portion of the patient 16. As discussed above in regard to FIG. 4, other types of jigs 100, such as straps, braces, and/or the like, may be used to secure the patient 16 in other embodiments.

Once the relevant portion of the patient 16 has been secured in a fixed position in process step 204, the sensor array 26 receives the output signals from the signal source(s) 28 coupled to the orthopaedic prosthesis 12. As discussed above in regard to FIG. 2, the sensor array 26 may be embodied as a magnetic sensor array 60 configured to sense or detect a magnetic field(s) generated by a magnetic signal source(s) 28. Alternatively, as discussed above in regard to FIG. 3, the sensor array 26 may be embodied as an antenna array 70 configured to receive output signals from a wireless transmitter signal source(s) 28. In some embodiments, such wireless transmitter signal source(s) 28 may be configured to transmit the output signals only while being inductively powered. In such embodiments, the patient support apparatus 14 may include a primary coil or the like to power the wireless transmitter signal source(s) 28. The primary coil may be controlled by, for example, the controller 30. Regardless, the output signals generated by the signal source(s) 28 are received by the sensor array 26 in process step 206.

Once the sensor array 26 receives the output signals from the signal source(s) 28, the controller 30 determines the position of the orthopaedic prosthesis 12, or component(s) thereof, relative to the patient support apparatus 14 in process step 208. To do so, the controller 30 receives data signals from the sensor array 26 indicative of the position of the orthopaedic prosthesis 12 relative to the sensor array 26. The controller 30 is configured to determine the position of the orthopaedic prosthesis 12 based on such data signals. The controller 30 may use any suitable algorithm to determine the position of the orthopaedic prosthesis 12. For example, in embodiments wherein the sensor array 26 is embodied as a magnetic sensor array 60, the controller 30 may be configured to execute an optimization algorithm. That is, the controller 30 may determine an initial estimate of the position (e.g., the six degrees of freedom) of the magnetic signal source(s) 28, determine theoretical magnetic field components of the three-dimensional magnetic flux density of the magnetic signal source(s) 28 based on the estimated position, and calculate the sum of errors between the theoretical magnetic field components and the measure magnetic field components of the magnetic signal source as measured by the magnetic sensor array 60. Such a calculation process may then be repeated using an adjusted estimated position of the magnetic signal source(s) 28 until the sum of errors is less than some predetermined threshold value. Once the sum of errors is less than the predetermined threshold value, the position of the magnetic signal source(s) has been determined. Because the position of the magnetic sensor array 60 relative to the patient support apparatus 14 is known, the position of the magnetic signal source(s) 28 relative to the patient support apparatus 14 may be determined by extrapolation.

One example of such an optimization algorithm which may be used by the controller 30 to determine the position of the magnetic signal source(s) is described in detail in U.S. patent application Ser. No. 11/323,609, entitled "APPARATUS AND METHOD FOR REGISTERING A BONE OF A PATIENT WITH A COMPUTER ASSISTED ORTHOPAEDIC SURGERY SYSTEM", which was filed on Dec. 30, 2005 by Jason T. Sherman et al.; in U.S. patent application Ser. No. 11/323,963, entitled "SYSTEM AND METHOD FOR REGISTERING A BONE OF A PATIENT WITH A COMPUTER ASSISTED ORTHOPAEDIC SURGERY SYSTEM," which was filed on Dec. 30, 2005 by Jason T. Sherman et al.; in U.S. patent application Ser. No. 11/323, 610, entitled "MAGNETIC SENSOR ARRAY," which was filed on Dec. 30, 2005 by Jason T. Sherman et al.; and in U.S. patent application Ser. No. 11/323,537, entitled "METHOD FOR DETERMINING A POSITION OF A MAGNETIC SOURCE," which was filed on Dec. 30, 2005 by Jason T. Sherman et al., the entirety of all of which is expressly incorporated herein by reference.

Alternatively, in embodiments wherein the sensor array 26 is embodied as an antenna array 70, the controller 30 may be configured to execute a radio frequency (RF) direction finding algorithm. Because each of the coplanar antennas 72, 74, 76 and non-coplanar antenna 78 is positioned at a different location with respect to the orthopaedic prosthesis (i.e., with respect to the wireless transmitter signal source(s) 28 coupled to the prosthesis 12), the data signals received from each antenna 72, 74, 76, 78 are different to varying amounts. As such, the location of the wireless transmitter signal source(s) 28, and therefore the location of the orthopaedic prosthesis 12, may be determined by comparing a portion or all of the data signals received form the antennas 72, 74, 76, 78. To do so, the controller 30 may use any radio frequency direction finding algorithm capable of determining data indicative of the location of the wireless transmitter signal source(s) 28 based on the data signals received from the antenna array 70. For example, the controller 30 may determine the location of the wireless transmitter signal source(s) 28 by comparing or otherwise analyzing the amplitudes of the various data signals, the phase of the data signals, the Doppler frequency shift of the data signals, the differential time of arrival of the data signals, and/or any other radio frequency direction finding methodology usable to determine the location of the wireless transmitter signal source(s) 28.

One example of such a algorithm for determining the position of the orthopaedic prosthesis 12 (i.e., the wireless transmitter signal source(s) 28) is described in detail in U.S. patent application Ser. No. 11/391,840, entitled "SYSTEM AND METHOD FOR DETERMINING A LOCATION OF AN ORTHOPAEDIC MEDICAL DEVICE," which was filed on Mar. 29, 2006 by Edward J. Caylor III, et al. and in U.S. patent application Ser. No. 11/392,001, entitled "SYSTEM AND METHOD FOR MONITORING KINEMATIC MOTION OF A PATIENT," which was filed on Mar. 29, 2006 by Edward J. Caylor III, the entirety of each of which is expressly incorporated herein by reference.

Once the position (e.g., the location and orientation) of the orthopaedic prosthesis 12 (i.e., the position of the signal source(s) 28) has been determined in process step 208, data indicative of such position(s) is stored in process step 210. The position data may be stored, for example, in the memory device 38. Additionally or alternatively, the position data may be transferred to and stored in the database 40 via the communication links 42. Once the position data has been stored, the controller 30 displays indicia of the position of the orthopaedic prosthesis 12, or components thereof, on the display device 24 and/or the display device 48 in process step 212. The controller 30 displays the indicia of the position of the orthopaedic prosthesis 12 relative to the patient support platform 18. Such indicia may be embodied as, for example, a graph, table, a number of images, data values, and/or the like. In one particular embodiment, the controller 30 is configured to display an image of the orthopaedic prosthesis 12 in a location and orientation determined based on the position data.

Once indicia of the position of the orthopaedic prosthesis 12, or components thereof, has been displayed in process step 212, the controller 30 determines if the orthopaedic healthcare provider desires to display historical position data. The orthopaedic healthcare provider may instruct the controller 30 to display the historical position data by supplying the appropriate commands via the remote control panel 44. Alternatively, the controller 30 may be configured to always display the historical position data. If the controller 30 determines that the orthopaedic healthcare provider does not desire to display the historical position data, the algorithm 200 loops back to process step 202. However, if the controller 30 is configured or instructed to display the historical position data, the algorithm 200 advances to process step 216 in which the controller 30 retrieves the historical position data from a storage device. For example, the controller 30 may retrieve the historical position data form the database 40. It should be appreciated that the historical position data is embodied as data indicative of the position of the orthopaedic prosthesis 12 and/or relevant bones of the patient 16 as determined during one or more previous examinations using the system 10.

Once the controller 30 has retrieved the historical position data of the orthopaedic prosthesis 12, or components thereof, the controller 30 is configured to display indicia of the historical position(s) of the orthopaedic prosthesis 12 on the display device 24 and/or display device 48. The indicia of the historical position(s) may be displayed contemporaneously with the indicia of the present position of the orthopaedic prosthesis 12 such that the orthopaedic healthcare provider may perform a comparison between the historical potions(s) and present position of the orthopaedic prosthesis 12 to determine the presence and extent of any implant migration and/or subsidence. In addition, the indicia of the historical position(s) may be displayed in a manner to identify that the data is historical rather than present. For example, the indicia of the historical position(s) of the orthopaedic prosthesis 12 may be displayed in a color or configuration that is different from the indicia of the present position of the prosthesis 12.

Figure 6:
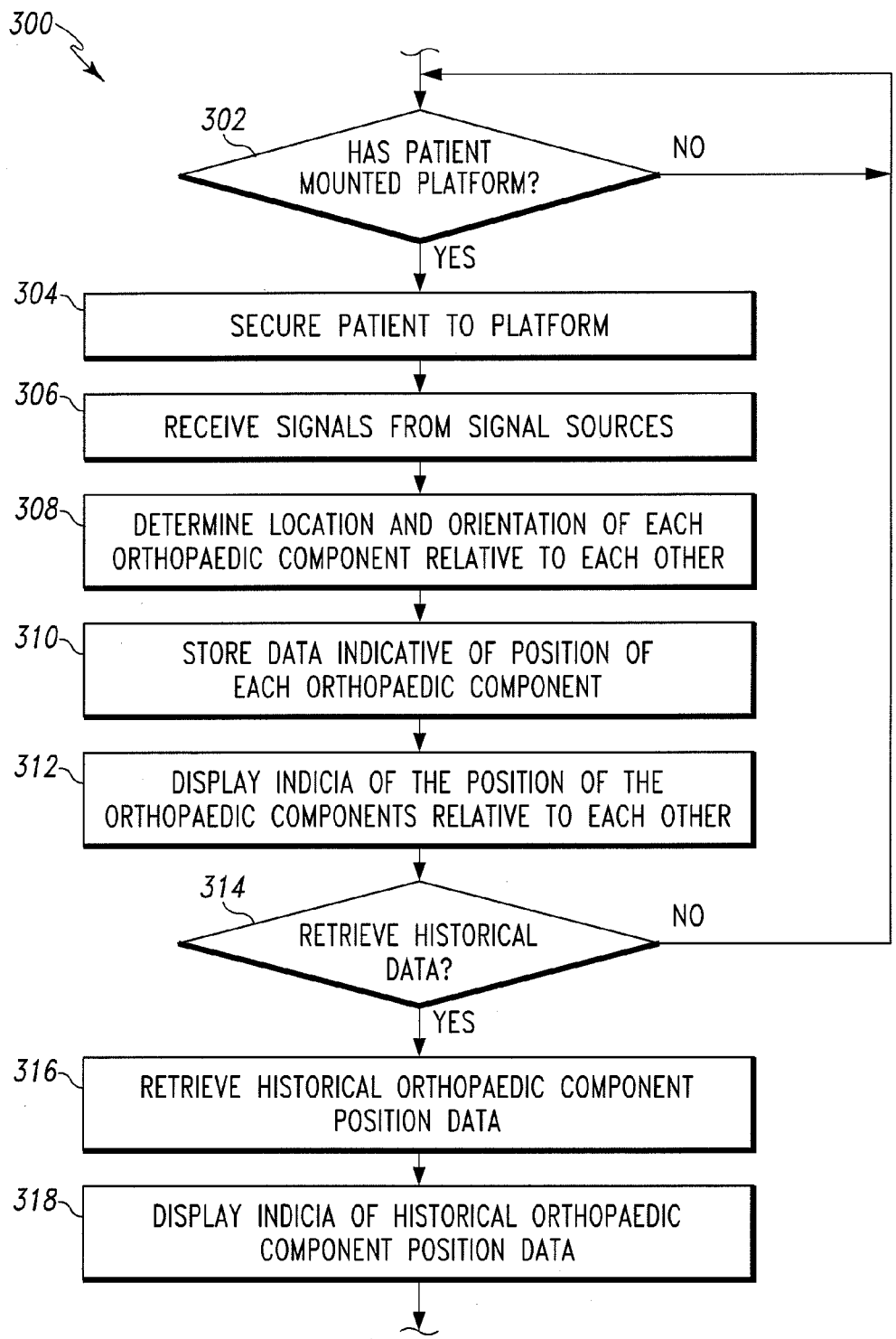
FIG. 6 is a simplified flowchart of another embodiment of an algorithm for determining a position of an orthopaedic prosthesis executed by the system of FIG. 1.

Referring now to FIG. 6, in embodiments wherein the controller 30 is configured to determine the position of individual components of the orthopaedic prosthesis 12 (e.g., a tibial component and a femoral component of an orthopaedic knee prosthesis) relative to each other, the controller 30 may be configured to execute an algorithm 300 for determining the position of the components of the orthopaedic prosthesis 12. In such embodiments, each component of interest of the orthopaedic prosthesis 12 includes one or more signal sources 28 coupled thereto. As discussed above in regard to FIGS. 1-3, such signal sources 28 may be embodied as a number of magnetic sources or a number of wireless transmitters.

The algorithm 300 beings with a process step 302 in which the controller 30 determines if the patient 16 has mounted the patient support platform 18. As discussed above in regard to algorithm 200, the patient support platform 18 may include a number of sensors for detecting when the patient 16 has mounted the platform 18 and/or the controller 30 may be instructed that the patient 16 has successfully mounted the platform 18 by the orthopaedic healthcare provider. Once the controller 30 has determined that the patient 16 has mounted the patient support platform 18, the patient 16 is secured in a fixed position on the platform 18 in process step 304. The patient 16 is secured in the fixed position via use of the jigs 100 as discussed above in regard to process step 204 of algorithm 200. The sensor array 26 subsequently receives the output signals from the signal source(s) 28 coupled to the individual components of the orthopaedic prosthesis 12 in process step 306. Again, as discussed above in regard to FIG. 2, the sensor array 26 may be embodied as a magnetic sensor array 60 configured to sense or detect a magnetic field(s) generated by a magnetic signal source(s) 28 or an antenna array 70 configured to receive output signals from a wireless transmitter signal source(s) 28 as discussed above in regard to FIG. 3.

Once the sensor array 26 receives the output signals from the signal source(s) 28, the controller 30 determines the position of each relevant component of the orthopaedic prosthesis 12 relative to each other in process step 308. To do so, the controller 30 receives data signals from the sensor array 26 indicative of the position of the components of the orthopaedic prosthesis 12 relative to the sensor array 26. The controller 30 is configured to determine the position of each relevant component of the orthopaedic prosthesis 12 based on such data signals. The controller 30 may use any suitable algorithm to determine the position of the components of the orthopaedic prosthesis 12. For example, in embodiments wherein the sensor array 26 is embodied as a magnetic sensor array 60, the controller 30 may be configured to execute an optimization algorithm as discussed in more detail above in regard to process step 208 of algorithm 200. Alternatively, in embodiments wherein the sensor array 26 is embodied as an antenna array 70, the controller 30 may be configured to execute a radio frequency (RF) direction finding algorithm as also discussed above in regard to process step 208 of algorithm 200. Regardless, the controller 30 determines the position of each component of the orthopaedic prosthesis 12 relative to each other.

Once the controller 30 has determined the position of each relevant component, the controller 30 is configured to store data indicative of such positions in process step 310. The position data may be stored, for example, in the memory device 38 and/or database 40. Because the controller 30 is configured to determine the position of each component relative to each other, the controller 30 may store the position data in a relative form. For example, the controller 30 may store position data for an initial component and store position data for each subsequent component in a data form relative to the initial form such as, for example, in a vector format. Once the position data has been stored, the controller 30 displays indicia of the position of each relevant component of the orthopaedic prosthesis relative to each other on the display device 24 and/or the display device 48 in process step 312. Such indicia may be embodied as, for example, a graph, table, a number of images, data values, and/or the like.

Once indicia of the position of the orthopaedic prosthesis 12, or components thereof, has been displayed in process step 312, the controller 30 determines if the orthopaedic healthcare provider desires to display historical position data in process step 314. If so, the algorithm 300 advances to process step 316 in which the controller 30 retrieves the historical position data from a storage device such as, for example, the memory device 38 and/or the database 40. Again, the historical position data is embodied as data indicative of the position of the components of the orthopaedic prosthesis 12 as determined during one or more previous examinations using the system 10.

Once the controller 30 has retrieved the historical position data of the relevant components of the orthopedic prosthesis 12, the controller 30 is configured to display indicia of the historical position(s) of the orthopaedic prosthesis 12 components on the display device 24 and/or display device 48. The indicia of the historical position(s) may be displayed contemporaneously with the indicia of the present position of the components of the orthopaedic prosthesis 12 such that the orthopaedic healthcare provider may perform a comparison between the historical position(s) and present position of the components to determine the presence and extent of any implant migration and/or subsidence.

Figure 7:
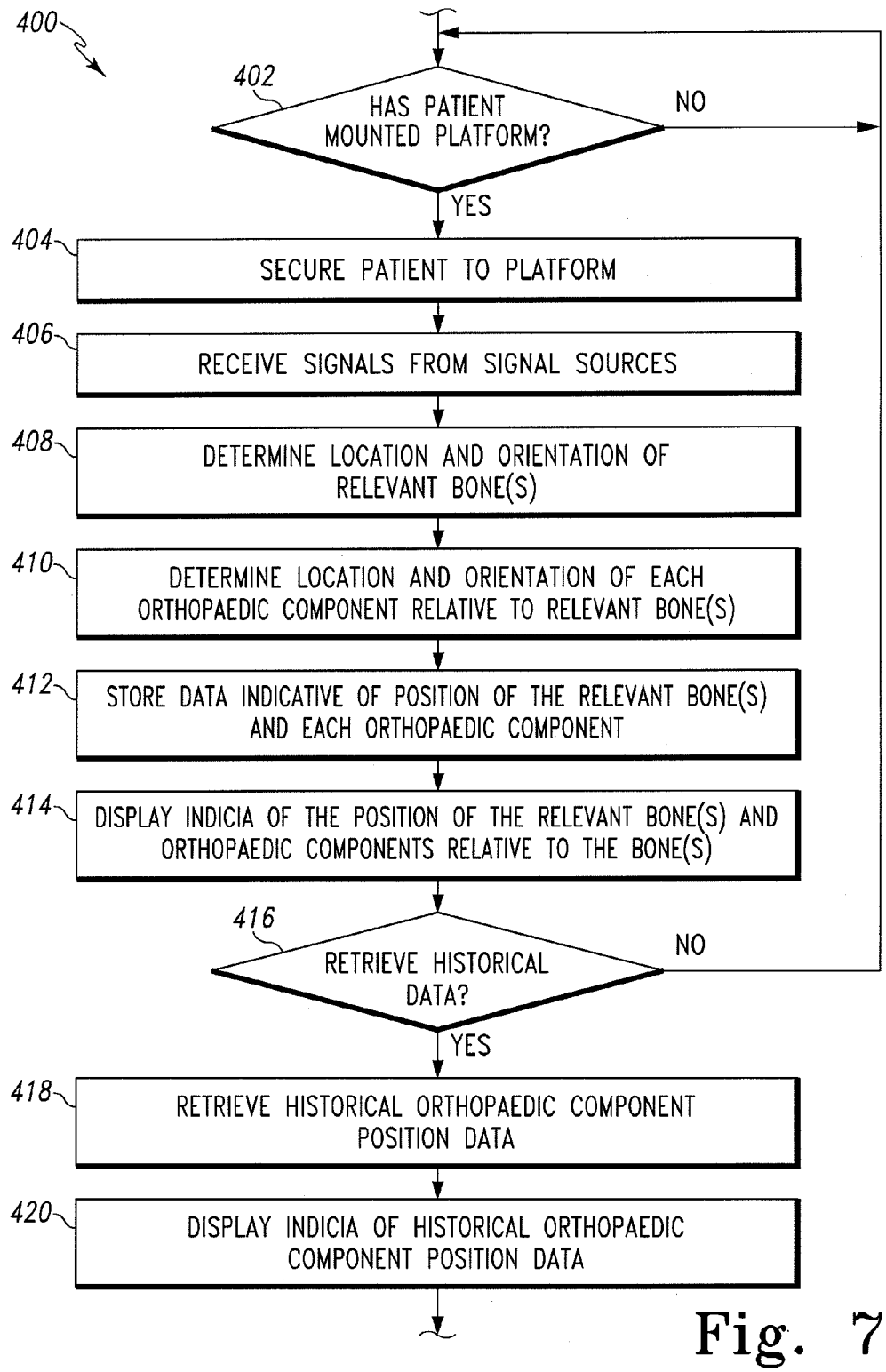
FIG. 7 is a simplified flowchart of a further embodiment of an algorithm for determining a position of an orthopaedic prosthesis executed by the system of FIG. 1.

Referring now to FIG. 7, in embodiments wherein the controller 30 is configured to determine the position of the orthopaedic prosthesis 12, or components thereof, relative to the bone(s) of the patient 16, the controller 30 may be configured to execute an algorithm 400 for determining the position of the orthopaedic prosthesis 12 and relevant bone(s) of the patient 16. In such embodiments, each component of interest of the orthopaedic prosthesis 12 and each relevant bone of the patient 16 includes one or more signal sources 28 coupled thereto. As discussed above in regard to FIGS. 1-3, such signal sources 28 may be embodied as a number of magnetic sources or a number of wireless transmitters.

The algorithm 400 beings with a process step 402 in which the controller 30 determines if the patient 16 has mounted the patient support platform 18. As discussed above in regard to algorithm 200, the patient support platform 18 may include a number of sensors for detecting when the patient 16 has mounted the platform 18 and/or the controller 30 may be instructed that the patient 16 has successfully mounted the platform 18 by the orthopaedic healthcare provider. Once the controller 30 has determined that the patient 16 has mounted the patient support platform 18, the patient 16 is secured in a fixed position on the platform 18 in process step 404. The patient 16 is secured in the fixed position via use of the jig 100 as discussed above in regard to process step 204 of algorithm 200. The sensor array 26 subsequently receives the output signals from the signal source(s) 28 coupled to the individual components of the orthopaedic prosthesis 12 in process step 406. Again, as discussed above in regard to FIG. 2, the sensor array 26 may be embodied as a magnetic sensor array 60 configured to sense or detect a magnetic field(s) generated by a magnetic signal source(s) 28 or an antenna array 70 configured to receive output signals from a wireless transmitter signal source(s) 28 as discussed above in regard to FIG. 3.

Once the sensor array 26 receives the output signals from the signal source(s) 28, the controller 30 determines the position (i.e., location and orientation) of each relevant bone of the patient 16 (e.g., each bone having one or more components of the orthopaedic prosthesis 12 coupled thereto). To do so, the controller 30 receives data signals from the sensor array 26 indicative of the position of the relevant bone(s) of the patient 16 relative to the sensor array 26. The controller 30 is configured to determine the position of each relevant component of the orthopaedic prosthesis 12 based on such data signals. The controller 30 may use any suitable algorithm to determine the position of the bone(s) of the patient 16 such as the optimization algorithm or radio frequency (RF) direction finding algorithm described above in regard to FIGS. 2 and 3 respectively depending upon the particular embodiment of the sensor array 26. Once the controller 30 has determined the position of the relevant bone(s) of the patient 16, the controller 30 determines the position of the relevant components of the orthopaedic prosthesis 12 in process step 410. The controller 30 is configured to determine the position of the components of the prosthesis 12 relative to the position of the relevant bone(s) of the patient 16. Similar to process step 308 of algorithm 300, the controller 30 may use any suitable algorithm to determine the position(s) of the relevant components of the orthopaedic prosthesis 12.

Once the controller 30 has determined the position of each relevant bone and orthopaedic prosthesis 12 components, the controller 30 is configured to store data indicative of such positions in process step 412. The position data may be stored, for example, in the memory device 38 and/or database 40. Again, as discussed above in regard to process step 310 of algorithm 300, the controller 30 may store the position data in a relative form. For example, the controller 30 may store the position data for the component(s) of the orthopaedic prosthesis 12 in a relative form or format based on the position of the relevant bone(s) of the patient 16 as determined in process step 408. Once the position data has been stored, the controller 30 displays indicia of the position of each relevant bone of the patient 16 on the display device 24 and/or the display device 48 in process step 414. In addition, the controller 30 also displays indicia of the position of each relevant component of the orthopaedic prosthesis 12 in process step 414. The controller 30 displays the indicia of the positions of the components of the orthopedic prosthesis 12 relative to the relevant bone(s) of the patient 16. Such indicia may be embodied as, for example, a graph, table, a number of images, data values, and/or the like.

Once indicia of the positions of the relevant bones and orthopaedic prosthesis 12 components has been displayed in process step 414, the controller 30 determines if the orthopaedic healthcare provider desires to display historical position data in process step 416. If so, the algorithm 400 advances to process step 416 in which the controller 30 retrieves the historical position data from a storage device such as, for example, the memory device 38 and/or the database 40. Again, the historical position data is embodied as data indicative of the position of the components of the orthopaedic prosthesis 12 as determined during one or more previous examinations using the system 10.

Once the controller 30 has retrieved the historical position data of the relevant components of the orthopedic prosthesis 12, the controller 30 is configured to display indicia of the historical position(s) of the relevant bone(s) of the patient 16 and the relevant components of the orthopaedic prosthesis 12 on the display device 24 and/or display device 48. The indicia of the historical position(s) may be displayed contemporaneously with the indicia of the present position of the bone(s) of the patient 16 and the components of the orthopaedic prosthesis 12 such that the orthopaedic healthcare provider may perform a comparison between the historical position(s) and present position of the components o determine the presence and extent of any implant migration and/or subsidence.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems, apparatuses, and methods described herein. It will be noted that alternative embodiments of the systems and methods of the present disclosure may not include all of the features described yet still benefit from at least some of the advantages of such features. Those of ordinary skill in the art may readily devise their own implementations of the systems, apparatuses, and methods that incorporate one or more of the features of the present invention and fall within the spirit and scope of the present disclosure as defined by the appended claims.

The invention claimed is:

1. An apparatus for monitoring the position of an orthopaedic prosthesis implanted in a body of a patient, the apparatus comprising:
a patient support platform configured to support a patient in a standing position, the patient support platform including a top planar surface;
a sensor array coupled to the patient support platform and configured to generate data signals in response to an output signal received from a signal source coupled to the orthopaedic prosthesis implanted in the body of the patient while the patient is supported by the patient support platform in the standing position, the sensory array including (i) a first directional antenna having a first boresight, (ii) a second directional antenna having a second boresight, (iii) a third directional antenna having a third boresight, each of the first, second, and third boresights being coplanar with each other, and (iv) a fourth directional antenna having a fourth boresight that is non-coplanar with the first, second, and third boresights, each of the first, second, third, and fourth boresights being directed toward a common volume of space;
a jig coupled to the patient support platform and comprising a first patient securing member located a first distance above the patient support platform and a second securing member located a second distance above the patient support platform substantially equal to the first distance, the first and second patient securing members being positionable to apply pressure in opposing directions to a portion of the body of the patient to secure the portion of the body of the patient (i) in a fixed position relative to the sensor array and (ii) within the common volume while the patient is standing on the patient support platform, the portion of the body of the patient having the orthopaedic prosthesis implanted therein; and
a controller electrically coupled to the sensor array and configured to determine the position of the orthopaedic prosthesis based on the data signals received from the sensor array.

2. The apparatus of claim 1, wherein the patient support platform comprises an enclosure and at least a portion of the controller is positioned in the enclosure.

3. The apparatus of claim 1, wherein each of the first, second, third, and fourth directional antennas is configured to generate data signals in response to an output signal received from a wireless transmitter coupled to the orthopaedic prosthesis.

4. The apparatus of claim 1, wherein the first, second, third, and fourth directional antennas are spiral directional antennas.

5. The apparatus of claim 1, wherein the controller is configured to determine the position of the orthopaedic prosthesis by comparing the data signals to each other.

6. The apparatus of claim 1 further comprising a display device coupled to the patient support platform and electrically coupled to the controller, wherein the controller is configured to display indicia of the location of the orthopaedic prosthesis on the display device.

7. The apparatus of claim 6, wherein the controller is further configured to retrieve position data indicative of a previously determined position of the orthopaedic prosthesis from a storage device and display indicia of the previously determined position of the orthopaedic prosthesis on the display device.

8. The apparatus of claim 1, wherein the first boresight, the second boresight, the third boresight, and the fourth boresight intersect each other in the common volume of space.

9. The apparatus of claim 1, wherein the first, second, and third directional antennas are coupled to the patient support platform such that when the patient is supported by the patient support platform in the standing position: the first directional antenna is located in front of the patient, the second directional antenna is located toward the left side of the patient, and the third directional antenna is located toward the right side of the patient.

10. The apparatus of claim 8, wherein the fourth directional antenna is coupled to the patient support platform such that the fourth directional antenna is located in front of the patient when the patient is supported by the patient support platform in the standing position.

* * * * *